United States Patent [19]

Forman et al.

[11] 4,194,715
[45] Mar. 25, 1980

[54] CONTAINER SUPPORT MEANS

[75] Inventors: Hugh M. Forman, Waukesha; Richard A. Rauschenberger, Brookfield, both of Wis.

[73] Assignee: G. D. Searle & Co., Skokie, Ill.

[21] Appl. No.: 864,179

[22] Filed: Dec. 27, 1977

[51] Int. Cl.² ............................................. A47K 1/08
[52] U.S. Cl. ............................ 248/311.1 R; 128/275
[58] Field of Search ............ 248/215, 359, 360, 318, 248/311.1, 95; 128/275, 295, 294; 4/110

[56] References Cited

U.S. PATENT DOCUMENTS

| | | | |
|---|---|---|---|
| 2,992,854 | 7/1961 | Berlin | 248/215 X |
| 3,033,377 | 5/1962 | Inman | 248/290 X |
| 3,332,653 | 7/1967 | Hoelzel | 248/311.1 X |
| 3,345,023 | 10/1967 | Scottetaw | 248/95 |
| 3,473,772 | 10/1969 | Nilson | 248/311.1 X |
| 3,529,598 | 9/1970 | Waldman et al. | 128/275 |
| 3,534,738 | 10/1970 | Huck | 248/95 X |
| 4,019,707 | 4/1977 | Quinn | 248/95 |
| 4,027,842 | 6/1977 | Mittleman | 248/318 X |

*Primary Examiner*—J. Franklin Foss
*Attorney, Agent, or Firm*—John A. Dhuey; James R. Hennes

[57] ABSTRACT

A container support useful for supporting flexible fluid containers in a suspended, upright position is described having a hinged arm with detented hinging means.

8 Claims, 8 Drawing Figures

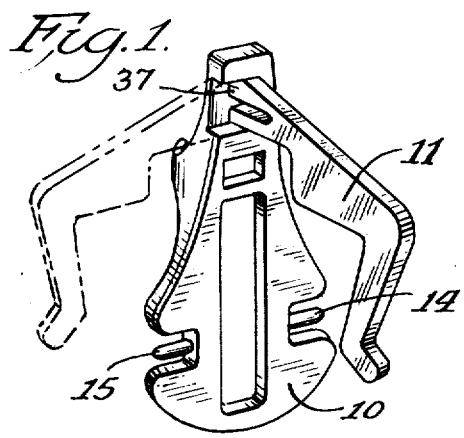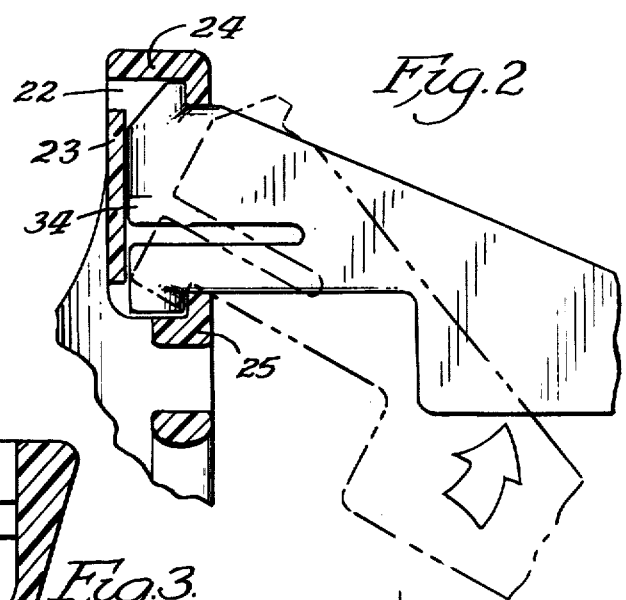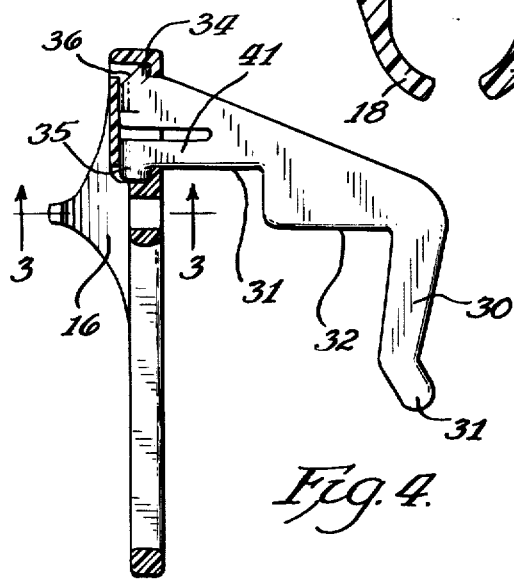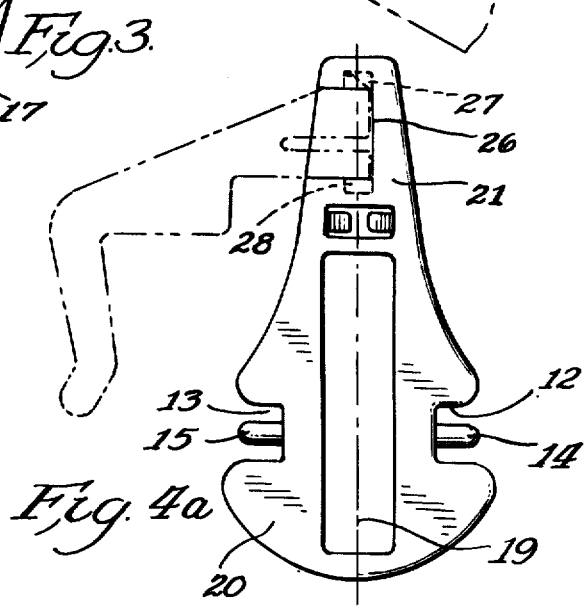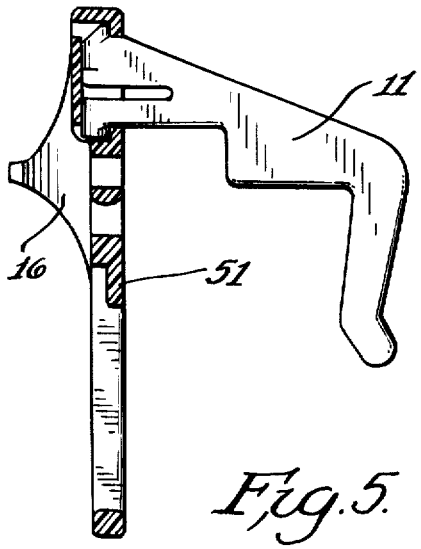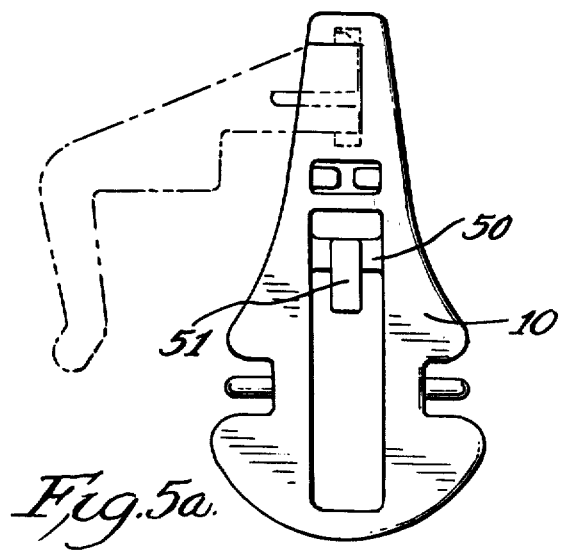

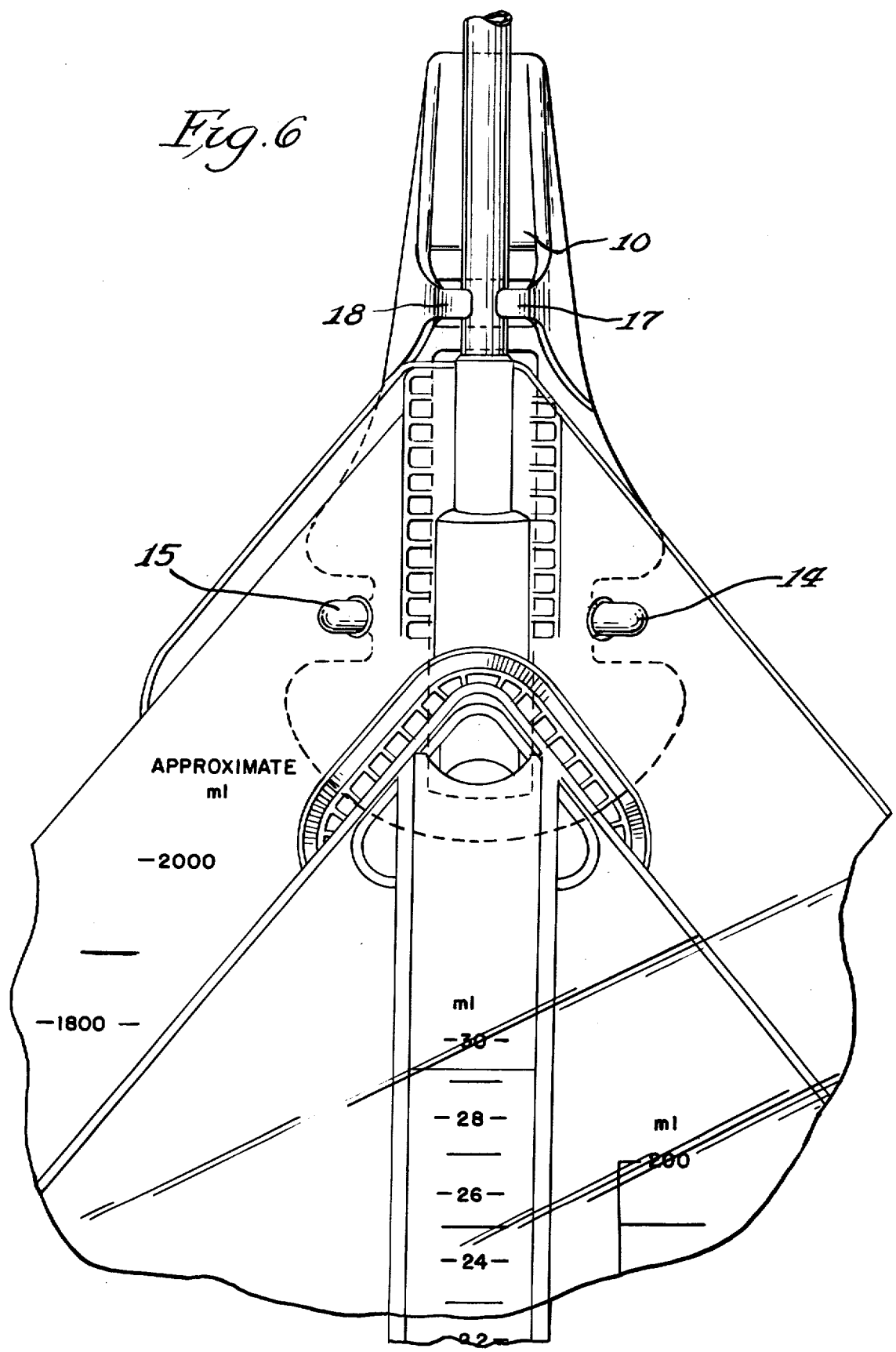

CONTAINER SUPPORT MEANS

This invention is concerned generally with support means for containers. More particularly, it is concerned with a hook to suspend and support flexible fluid collection containers in an upright position.

Flexible collection containers fabricated from plastic films are utilized in many applications to collect fluids from various sources. Such containers are not sufficiently rigid to support themselves in an upright position on surfaces during the collection process, and it is usually unsatisfactory to permit such containers to lie flat on a surface because of the potential problem of leakage through the fluid inlet port.

Furthermore, in certain applications, the amount of fluid collected at a particular time must be apparent. In order to have an accurate fluid volume reading, it is important that the container be supported during the collection process in a position substantially the same as when the container is calibrated.

A particular application where such considerations are extremely important is the collection of body fluids from hospital patients. Typically, during a urinary cathertization procedure a patient is connected to a fluid collection container and a continuous indication of the amount of fluid expelled is desired. Conventional urinary drainage bags are formed of flexible plastic film with volume indicia inscribed on an outer face of the container. A correct volume indication is provided when the bag is suspended in an upright position to permit fluid to accumulate first at the bottom of the bag with increasing volume of fluid moving the fluid level toward the top of the bag.

In applications where the patient is confined to bed, it is desirable to have a hook for attaching the bag to the bed of the patient to minimize the length of connective tubing and generally provide an area about the bed of the patient which allows free access to attending personnel without concern for obstacles such as a drainage bag stand and connective tubing.

It is especially desirable to hang the bag at approximately mattress support level and to have means for supporting the bag on a vareity of hospital bed designs. Prefered features are that the bag attach quickly to a bed or bed frame, that the combined support means and bag present minimum bulk in packaging, that the support means attach quickly and easily to a variety of bags, and that the entire support means and bag be economical enough to be disposable after a single use.

The present invention satisfying the above-noted requirements is illustrated by the following drawings in which:

FIG. 1 is a perspective view of the assembled container support;

FIG. 2 is a detailed view illustrating the manner of attachment of the support arm to the support body;

FIG. 3 is a sectional view along line 3—3 in FIG. 4;

FIG. 4 is a side sectional view of the container support;

FIG. 4a is a plan view of the container support;

FIG. 5 is a side sectional view of an alternate embodiment of the container support;

FIG. 5a is a plan view of the container support illustrated in FIG. 5; and

FIG. 6 is a detailed view of a particular manner of attaching the container support of this invention to a flexible container.

As illustrated by the drawings, the container support has a generally planar body 10 to which a support arm 11 is hingedly connected at its upper end. Body 10 is formed with recesses 12 and 13 in its outer edges and adjacent its lower end. Cylindrical appendages 14 and 15 extend outwardly from the sides of body 10 into recesses 12 and 13, respectively. Appendages 14 and 15 are adapted to be placed through holes formed in the top portion of a flexible collection container as shown in FIG. 6. Appendages 14 and 15 are appropriately spaced from the top and bottom edges of recesses 12 and 13, respectively, to accomodate the bulk of the flexible film of which the containers are usually formed. The front surface of body 10 diverges from the plane of body 10 at a point above appendages 14 and 15 to form arms 17 and 18 which provide a C-shaped tube clasp 16. As shown in FIG. 6, collection tubing passes through clasp 16 into the collection container suspended below. An opening 19 preferably is provided in body 10 to accomodate the tubing and container material surrounding it to facilitate hanging of the container in a vertical position. Lower portion 20 of body 10 preferably is of greater width than the top portion 21 so that the inlet area of the container remains flat when suspended from the support.

The top portion 21 of body 10 is provided with opening 22 to receive support arm 11. Opening 22 is defined by front wall 23, top wall 24, bottom wall 25 and side wall 26. Topwall 24 is formed with recess 27 and bottom wall 25 is formed with a recess 28 to receive support arm 11 in a manner which will be described hereinafter.

Support arm 11 is substantially planar having a main support section 29 and a depending hook section 30. Support section 29 is formed with flat portions 31 and 32 on the underside thereof. The lengths of flats 31 and 32 are chosen to accomodate various standard size bed rails and preferably are not equal to each other so that one hook can be used on different beds.

Hook section 30 depends downwardly from section 29 and preferably is inclined rearwardly with respect to the vertical position to facilitate retention of the hook on bed members. Section 30 is tapered towards its lower end 31, which is rounded, to provide easy insertion into openings present on the patient's bed.

The rearward end of support arm 11 is formed with an upstanding projection 34 and downwardly extending projection 35. Projections 34 and 35 are adapted to be retained in recesses 27 and 28, respectively. To facilitate insertion of support arm 11 into opening 22, projection 34 is provided with a leading inclined edge 36. Slot 40 permits projection 35 to be flexed toward projection 34 during insertion of support arm 11 into opening 22 to complete assembly of the hook. Integral cantilever spring arm 41 is formed by slot 40 and its strength is established to permit assembly but not allow detachment of arm 11 under load.

Support arm 11 can be rotated within opening 22 from a first position in which support arm 11 is in the same plane as body 10 (as shown by the dashed line in FIG. 1) to a second position in which support arm 11 is perpendicular to the plane of body 10 (as shown by the solid line in FIG. 1). The first position provides a compact, flat configuration for the assembled container support so that the support can be packaged alone or with the collection container in a package having minimal depth. When the assembled container support is to be used, support arm 11 is rotated from its first position to its second position whereat support arm 11 can be placed over a bed frame and supported on either of flats 31 or 32, or in an opening on or near the bed by insertion of hook portion 30 through the opening.

In an especially preferred embodiment of the invention, support arm 11 is provided with a nub 37 adjacent its rearward face. Nub 37 is dimensioned to contact semi-resilient wall 23 when support arm 11 is intermediate its first and second positions, thus providing a force which resists movement of support arm 11 away from its first position or its second position.

Wall 23 is semi-resilient so as to permit it to become distended by nub 37 to a certain extent as a support arm 11 is moved between its first and second positions. Accordingly, the cooperative action of nub 37 and wall 23 provides a detent which releasably locks support arm 11 in its first position and second position, respectively. In order for the detent action to be effective, the distance between wall 23 and the recesses 27 and 28 must be chosen to provide a springing action by wall 23 when support arm 11 is moved from its first position to its second position.

An alternate embodiment of the invention is illustrated in FIGS. 5 and 5a wherein an auxiliary support means is added for particular applications where the container support may be too rigid or insufficient size to permit direct attachment to a support near the patient or where the added security of tying of the container to a support is desired. The auxiliary support means is formed by a horizontal crossmember 50 extending across opening 19 and having a downwardly extending projection 51.

In use a continuous loop of string or other material can be placed about projection 51 and extended under cross-member 50, through opening 52 and over cross-member 50, over an available support near the patient and back about projection 51. The container remains suspended then by the container support which is attached to the string loop. Alternatively, the string loop can be formed with a ferrule adapted to receive projection 51 and the loop is passed over the support as described previously. This latter arrangement permits cutting of the string loop for tying attachment about a support wherein each of the individual tying members formed by the cutting operation are securely fastened to the container support at projection 51.

The invention has been illustrated with reference to the drawings. However it is not meant to be limited thereby and various modifications will be apparent to those skilled in the art without departing from the spirit and scope of the invention.

What is claimed is:

1. A support for a container comprising:
 a generally planar body having first and second opposed ends and a semi-resilient wall at its second end;
 means on said body adjacent said first end for attaching a container to said body;
 a support arm mounted on said body at said second end, said support arm being movable from a first position substantially in the plane of said body to a second position substantially perpendicular to the plane of said body; and
 means on said support arm for engaging said semi-resilient wall at positions intermediate said first position and said second position, whereby movement of said support arm relative to said body is resisted at said intermediate positions.

2. A support as in claim 1 wherein said engaging means comprises an outwardly extending nub on said support arm for engaging said wall.

3. A support as in claim 1 wherein said attachment means comprises rodlike appendages extending outwardly from the sides of said body for engagement with said container.

4. A support as in claim 1 wherein said body has an opening in the lower central portion thereof and further comprising tube retention means mounted on said body adjacent the upper end of said opening.

5. A support for a container comprising:
 a generally planar body having first and second opposed ends and having a rearwardly facing opening at its second end defined by a front wall, a top wall, a bottom wall and a side wall, said top wall having a first recess formed therein and said bottom wall having a second recess formed therein;
 means on said body adjacent said first end for attaching a container to said body; and
 a support arm hingedly mounted on the second end of said body within said opening, said support arm having an upwardly extending projection and a downwardly extending projection for engaging said recesses in said top and bottom wall respectively, whereby said support arm is movable from a first position substantially in the plane of said body to a second position substantially perpendicular to the plane of said body.

6. A support as in claim 5 wherein said front wall is semi-resilient and said support arm has an upstanding projection on the face thereof for engaging said semi-resilient wall when said support arm is moved from said first position to said second position.

7. A support as in claim 6 further comprising auxiliary hanging means on said body.

8. A support as in claim 7 wherein said body has an opening adjacent its first end and said auxiliary hanging means comprises a horizontal member extending across said opening and having a downwardly extending tab.

* * * * *